United States Patent [19]

Etcheverry et al.

[11] Patent Number: 4,940,661

[45] Date of Patent: Jul. 10, 1990

[54] METALLOTHIONEIN TRANSCRIPTION CONTROL SEQUENCES AND USE THEREOF

[75] Inventors: Tina M. Etcheverry, Berkeley; Ronald A. Hitzeman, Pacifica, both of Calif.

[73] Assignee: Genentech, Inc., South San Francisco, Calif.

[21] Appl. No.: 102,189

[22] Filed: Sep. 29, 1987

Related U.S. Application Data

[63] Continuation of Ser. No. 611,235, May 17, 1984, abandoned.

[51] Int. Cl.$^5$ .................. C12P 21/00; C12P 21/02; C12P 19/34
[52] U.S. Cl. .................. 435/69.1; 435/172.3; 435/254; 435/255; 435/320; 435/91; 435/256; 435/69.3; 435/69.4; 435/69.5; 435/69.6; 935/37; 935/69; 935/79; 935/60; 536/27
[58] Field of Search .............. 435/68, 70, 172.3, 255, 435/320, 948; 935/37; 536/27

[56] References Cited

FOREIGN PATENT DOCUMENTS

| | | | |
|---|---|---|---|
| 0078154 | 5/1983 | European Pat. Off. | 435/68 |
| 0096491 | 12/1983 | European Pat. Off. | 435/68 |
| 0134773 | 3/1985 | European Pat. Off. | 435/68 |
| 8301783 | 5/1983 | World Int. Prop. O. | 435/68 |

OTHER PUBLICATIONS

Etcheverry et al., Bio/Technology, 4:726–730 (1986).
Fogel et al., Proc. Natl. Acad. Sci. USA, 79: 5342–5346 (1982).
Karin et al., Proc. Natl. Acad. Sci. USA, 81: 337–341 (1984).
Welch et al., Mol. Cell. Biol., 3 (8): 1353–1361 (1983).
Welch et al., in The Molecular Biology of Yeast (eds. Hicks, Klar and Strathern) p. 249 (Cold Spring Harbor, New York) 1983.
Butt et al., Gene, 27: 23–33 (1984).
Anonymous, in Genetic Engineering News 3(2) p. 6 (1983).
Butt et al., Molecular Biology of Yeasts, (Cold Spring Harbor Laboratories: New York, 1983), p. 177, "Cloning of Copper-Inducible Genes in Yeast".
Butt et al., Molecular Biology of Yeasts, (Cold Spring Harbor Laboratories: New York, 1983), p. 178, "Copper Metallothionein of Yeast, a Model System for Gene Expression Studies".
Butt et al., 12th Intl. Conf. on Yeast, Edinburgh (R2) (1984) "The Copper Inducible Metallothionein of Yeast, Evolution of the Gene in Fungi".
Butt et al., Proc. Natl. Acad. Sci. USA, 81: 3332–3336 (1984).
Fogel et al., Current Genetics, 7: 347–355 (1983).
Genetic Technology News, Jan. 1983, p. 2 "Tandem Genes Cloned in Yeast Could Boost Protein Output".
Karin et al., Nature 299: 797–802 (1982).
Valenzuela et al., CSH Yeast Meeting in Aug. 1983. Abstract on p. 255 "The Structure of the Yeast CUP1 Locus and Its Use in the Regulation of the Expression of Foreign Proteins in Yeast".
Karin et al., Cell 36: 371–379 (1984).
Karin et al., Nature 308: 513–519 (1984).
Karin et al., DNA 3: 319–326 (1984).
Karin et al., Nature 286: 295–297 (1980).
Karin et al., Proc. Natl. Acad. Sci. USA 80: 4040–4044 (1983).
Durnam et al., J. Biol. Chem. 256: 5712–5716 (1981).
Hager et al., Nature 291: 340–342 (1981).
Searle et al., Mol. and Cell. Biol. 4: 1221–1230 (1984).

(List continued on next page.)

Primary Examiner—Robin L. Teskin
Attorney, Agent, or Firm—Janet E. Hasak

[57] ABSTRACT

Metallothionein transcription control sequences, promoters or inducing regions, free of DNA encoding metallothionein, are used to inducibly express genes encoding polypeptides of interest. Vectors and host expression systems using the transcription control sequences, promoters and/or inducing regions are provided.

14 Claims, 7 Drawing Sheets

OTHER PUBLICATIONS

Brinster et al., Nature 296: 39–42 (1982).
Palmiter et al., Science 222: 809–814 (1983).
Beach et al., Proc. Natl. Acad. Sci. USA 78: 2110–2114 (1981).
Mayo et al., (Cold Spring Harbor Laboratories: New York, 1982) pp. 67–73, "Gene Amplification", ed. R. T. Schinke.
Palmiter et al., Cell 29: 701–710 (1982).
Durnam et al., Proc. Natl. Acad. Sci. USA 77: 6511–6515 (1980).
Glanville et al., Nature 292: 267–271 (1981).
Carter et al., in *Current Communications in Molecular Biology* (eds. Gluzman and Shenk) pp. 170–174, (Cold Spring Harbor, N.Y.) 1983.
Valenzuela et al., in *The Molecular Biology of Yeast* (eds. Hicks, Klar and Strathern) p. 255 (Cold Spring Harbor, N.Y.) 1983.
Butt, *J. Cell Biochem. Supp.*, 7A: 384 (1984).

FIG. 6-1

```
                        hhaI
            haeII          ndeI                              ahaIII
CGATCCCATT ACCGACATTT GGGCGCTATA CGTGCATATG TTCATGTATG TATCTGTATT TAAAACACTT
GCTAGGGTAA TGGCTGTAAA CCCGCGATAT GCACGTATAC AAGTACATAC ATAGACATAA ATTTTGTGAA
-459
            mnlI                            fokI              hphI
TTGTATTATT TTTCCTCATA TATGTGTATA GGTTTATACG GATGATTTAA TTATTACTTC ACCACCCTTT
AACATAATAA AAAGGAGTAT ATACACATAT CCAAATATGC CTACTAAATT AATAATGAAG TGGTGGGAAA ddeI
       ecoRV
ATTTCAGGCT GATATCTTAG CCTTGTTACT AGTTAGAAAA AGACATTTTT GCTGTCAGTC ACTGTCAAGA
TAAAGTCCGA CTATAGAATC GGAACAATGA TCAATCTTTT TCTGTAAAAA CGACAGTCAG TGACAGTTCT xbaI
hinfI          mboII        sfaNI         hgaI
GATTCTTTTG CTGGCATTTC TTCTAGAAGC AAAAAGAGCG ATGCGTCTTT TCCGCTGAAC CGTTCCAGCA
CTAAGAAAAC GACCGTAAAG AAGATCTTCG TTTTTCTCGC TACGCAGAAA AGGCGACTTG GCAAGGTCGT
                      -230
                                hinfI
AAAAAGACTA CCAACGCAAT ATGGATTGTC AGAATCATAT AAAAGAGAAG CAAATAACTC CTTGTCTTGT
TTTTTCTGAT GGTTGCGTTA TACCTAACAG TCTTAGTATA TTTTCTCTTC GTTATTGAG GAACAGAACA
                                   TATA BOX
         mboII                                        taqI
ATCAATTGCA TTATAATATC TTCTTGTTAG TGCAATATCA TATAGAAGTC ATCGAAATAG ATATTAAGAA
TAGTTAACGT AATATTATAG AAGAACAATC ACGTTATAGT ATATCTTCAG TAGCTTTATC TATAATTCTT
             TATA BOX
      rsaI                            START
AAACAAACTG TACAATCAAT CAATCAATCA TCACATAAAA TGTTCAGCGA ATTAATTAAC TTCCAAAATG
TTTGTTTGAC ATGTTAGTTA GTTAGTTAGT AGTGTATTTT ACAAGTCGCT TAATTAATTG AAGGTTTTAC fnu4HI
                      bbvI
                alul                                             fnu4HI
                                                                 bbvI
                                                                 aluI
AAGGTCATGA GTGCCAATGC CAATGTGGTA GCTGCAAAAA TAATGAACAA TGCCAAAAAT CATGTAGCTG
TTCCAGTACT CACGGTTACG GTTACACCAT CGACGTTTTT ATTACTTGTT ACGGTTTTA GTACATCGAC fnu4HI
                                         mboII            bbvI
CCCAACGGGG TGTAACAGCG ACGACAAATG CCCCTGCGGT AACAAGTCTG AAGAAACCAA GAAGTCATGC
GGGTTGCCCC ACATTGTCGC TGCTGTTTAC GGGGACGCCA TTGTTCAGAC TTCTTTGGTT CTTCAGTACG STOP                                                  ahaIII
TGCTCTGGGA AATGAAACGA ATAGTCTTTA ATATATTCAT CTAACTATTT GCTGTTTTTA ATTTTAAAA
ACGAGACCCT TTACTTTGCT TATCAGAAAT TATATAAGTA GATTGATAAA CGACAAAAAT TAAAAATTTT taqI  hinfI ddeI        rsaI
GGAGAAGGAA GTTAATCGA CGATTCTACT CAGTTTGAGT ACACTTATGT ATTTTGTTTA GATACTTTGT
CCTCTTCCTT CAATTAGCT GCTAAGATGA GTCAAACTCA TGTGAATACA TAAAACAAAT CTATGAAACA accI                                       ndeI
TAATTTATAG GTATACGTTA ATAATTAAGA AAAGGAAATA AAGTATCTCC ATATGTCGCC CCAAGAATAA
ATTAAATATC CATATGCAAT TATTAATTCT TTTCCTTTAT TTCATAGAGG TATACAGCGG GGTTCTTATT
```

```
                                                                    taqI
                                                         hinfI      asuII
AATATTATTA CCAAATTCTA GTTTGCCTAA CTTACAACTC TGTATAGAAT CCCCAGATTT CGAATAAAAA
TTATAATAAT GGTTTAAGAT CAAACGGATT GAATGTTGAG ACATATCTTA GGGGTCTAAA GCTTATTTTT rsaI
                      kpnI
           aluI       banI
AAAAAAAAAA AGCTATTCAT GGTACC
TTTTTTTTTT TCGATAAGTA CCATGG
```

FIG. 6-2

METALLOTHIONEIN TRANSCRIPTION CONTROL SEQUENCES AND USE THEREOF

This application is a continuation of application Ser. No. 06/611,235, now abandoned, filed May 17, 1984.

BACKGROUND

This application relates to inducible transcription control sequences (TCS). In particular, it relates to inducible TCS for metallothionein (hereinafter "MT"), specifically yeast MT.

With the advent of recombinant DNA research, the need has arisen for strong and efficient promoters to direct the synthesis of proteins in microbial culture.

Yeast organisms are well suited for commercial expression of heterologous proteins, having advantages over tissue culture and bacteria. First of all, highly developed technology exists for yeast fermentation processes. Yeast can be employed safely since handling and disposal methods are well established. In addition, yeast is an eukaryotic organism which has advantages when expressing genes originating from other eukaryotic backgrounds. Most of all, yeast is extremely well characterized and can be manipulated genetically to maximize expression of heterologous peptides.

The ideal expression system for yeast as a microbial "factory" would allow for enhanced protein production, controlled during portions of the fermentation process. Products are currently made utilizing multicopy plasmids, efficient promoters and amplified genes. However, these systems still lack the ideal parameter, which involves the ability to direct product synthesis at a specific time during the fermentation. By divorcing the growth process (which may involve days of culture incubation) from that of product synthesis (which occurs within hours), one can obtain higher levels of product. The product is exposed to less time in the media or within cells where it may be susceptible to proteolytic degradation, and any detrimental effect of the product on the growth of the organism is removed by largely separating the growth and production processes. Controllable promoters will lead to efficient cell recycling and product harvesting during continuous culturing of cells.

We have found that MT TCS (specifically copper chelatin from yeast) are useful for this type of application. Metallothionein is known to be rapidly induced by the addition of copper ions to the media. Within ten minutes of exposure to copper the promoter is functioning maximally and the culture is synthesizing MT. The copper inducibility is retained on autonomously replicating plasmids in yeast.

For the purposes herein, TCS is defined as the combination of a promoter with a metal ion inducing region.

Publications which should be consulted in regard to the disclosures herein are Fogel et al., 1982, "P.N.A.S.-(USA)" 79:5342–5346; Carter et al., 1983, in *Current Communications in Molecular Biology* (eds. Gluzman, Y. and Shenk, T.) p. 170 (Cold Spring Harbor, N.Y.); Valenzuela et al., 1983, in *The Molecular Biology of Yeast* (eds. Hicks, J. B., Klar, A. and Strathern, J. N.) p. 255 (Cold Spring Harbor, N.Y.); Butt, 1983, "J. Cell Biochem. Supp." 7A: 384; Butt et al., 1984, "Gene" 27:23–33; Anonymous, in *Genetic Engineering News* 3(2) p. 6 (1983); Baxter et al., European Pat. Application 78,154; Fogel et al., European Patent Application 96,491; Welch et al., 1983 in *The Molecular Biology of Yeast* (eds. Hicks, J. B., Klar, A. and Strathern, J. N.) p. 249 (Cold Spring Harbor, N.Y.), p. 249; Welch et al., 1983, "Mol. Cell Biol." 3 (8): 1353–1361; and Karin et al., 1984 "P.N.A.S. (USA)" 81: 337–341.

SUMMARY OF THE INVENTION

An MT TCS has been identified and sequenced. This TCS contains both the transcriptional promoter and the metal ion regulatory region. The regions of the TCS responsible for promoter and regulatory functions have been localized. Accordingly, novel compositions are provided which comprise an MT promotor, an MT metal ion regulatory region, or an MT promoter under the control of a metal ion regulatory region, all of which are free of DNA encoding MT.

These compositions are employed to regulate the expression of polypeptides other than MT, e.g. other yeast or eukaryotic polypeptides.

Replicable vectors containing DNA encoding such other polypeptides under the transcriptional control of the MT promoter or metal ion regulatory region, or the two together as a TCS, are used to transform suitable MT synthesizing hosts such as yeast, the transformants cultured in the presence of inducing metal ions, and the desired polypeptide recovered. Contrary to the teachings of the art, the genes encoding non-MT polypeptides need not be tandemly iterated in the chromosomes under selection pressure in order to obtain elevated yields of the polypeptide. The genes instead can be placed in replicons such as autonomously replicating vectors (minichromosomes) or plasmids devoid of regions encoding active MT. We have found that it is not necessary to transform hosts with "linked" vectors in which a discrete promoter and a structural gene encoding the polypeptide of interest are ligated to a gene encoding active MT.

BRIEF DESCRIPTION OF THE DRAWINGS

FIG. 6 is the nucleotide sequence of the chelatin structural gene, promoter, regulatory region and 3'flanking region.

DETAILED DESCRIPTION OF THE INVENTION

Figure 1:
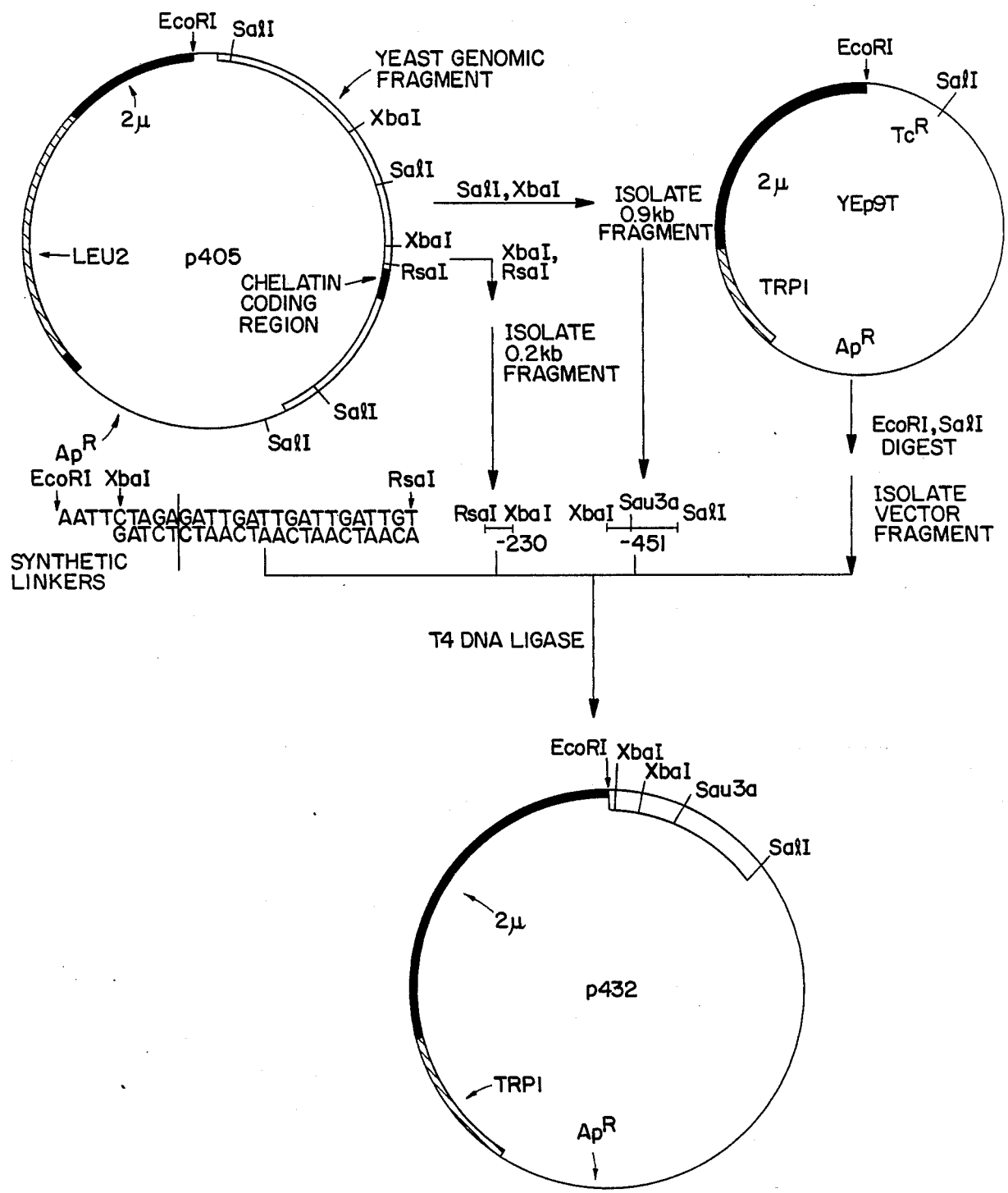
FIG. 1 illustrates the construction of a vector containing an MT TCS which is suitable for ligation to a gene expressing a polypeptide of interest.

The MTs as defined herein are small molecular weight proteins which chelate or bind heavy metals, protecting the cells against the toxic effects of such metals. These heavy metals include zinc, cadmium, copper and mercury. MTs are ubiquitously distributed in nature and have been identified in a broad range of eukaryotic species. The MT present in yeast has been designated copper-chelatin to distinguish it as a solely copper inducible protein.

All MTs identified are characteristically cysteine rich and lack aromatic amino acids. The cysteine residues provide the functional groups which bind copper in a stochiometry of 2:1. The locations of these residues within the protein are highly conserved between different species showing a tight evolutionary relationship.

The language "free of DNA encoding MT" as used herein means that no DNA is present which encodes MT having protective effect for host cells. DNA may be included which encodes a non-protective, non-chelating MT, as for example a mutant MT. In the preferred embodiment, however, the MT TCS is free of a mutant MT coding region for inactive MT.

The TCS for yeast MT, alternatively known as chelatin, is embraced within a 459 bp region upstream from the chelatin start codon. See FIG. 6 for sequence data. This region in turn consists of two functionally discrete units. The 230 bp region upstream (−230) from the start codon contains the chelatin promoter, including transcription initiation and ribosome binding sites. This is a useful promoter in its own right, but without more it is not induced by metal ions.

The additional sequence required to induce the MT promoter is found within the region located 229 bp upstream from the −230 promoter region or in conjunction with this 230 bp region. This additional sequence is designated the metal ion regulatory or inducer region. The metal ion regulatory region, upon transformation into yeast, is activated in an unknown fashion by the presence of copper ions in the medium. "Activation" in this context means that the messenger RNA produced from genes under the control of the TCS containing the metal ion regulatory region is increased in comparison to the same TCS without the metal ion regulatory region.

It should be noted that neither the promoter nor metal ion regulatory region necessarily occupies the entire sequence. These sequences were selected because they were flanked by convenient restriction enzyme sites, not because they function in toto as the promoter or regulatory regions. Accordingly, it is contemplated that the the promoter and regulatory functions may be more specifically resolved within the TCS fragments by methods known per se if that should be so desired. Such resolved sequences are within the scope herein.

The metal ion inducing region is useful when ligated to other, non-MT promoters which are recognized (transcribed) by the desired host. Examples include promoters from procaryotes, but yeast promoters such as α-factor, those from glycolytic genes, PGK, alcohol dehydrogenase, acid phosphatase, elongation factor I or those from invertase genes are preferred. The ligations of exogenous promoters to the inducing region may be accomplished readily by ligating the portions of the TCS responsible for induction, i.e., at least the XbaI-SalI or XbaI-Sau3a region shown in FIG. 1, into a position upstream from the desired promoter. The MT TCS, promoter or regulatory region need not have the nucleotide sequence set forth in FIG. 6. Any mutation (substitution, deletion or insertion), of the TCS, e.g. the 10 bp substitution disclosed in Example 1, may be employed which yields a TCS functional in promoting and/or inducing the MT gene in yeast strains.

The MT promoter, TCS or regulatory region is ligated to the gene of interest. Preferably this gene is the structural gene alone, free of the promoter or other 5' sequences native to the structural gene. However, the structural gene need not encode the mature polypeptide only, but in fact may encode pre, pro or prepro domains as well. These genes encode non-yeast eukaryotic or yeast homologous proteins. Examples include hepatitis B surface antigen (HB$_s$ Ag), tissue plasminogen activator (tPA), factor VIII, human growth hormone (hGH), or lymphotoxin.

The hosts suitable for use with the vectors of this invention are preferably yeast. In the case of hosts containing the metal ion regulatory region, where the host will be exposed to potentially toxic levels of metal ion as part of the induction of the region, the host should contain the active MT gene to ensure satisfactory growth. This active gene may be contained endogenously in the chromosome, or supplied on a replicating vector. The amounts of metal ion to be used for induction will exceed about 0.1 mM and can range up to about 10 mM in the fermenter.

Vectors which can be employed with the MT TCS generally will contain, in addition to the gene to be expressed and the TCS or promoter, (a) sequences enabling the vector to replicate in the host, e.g., an autonomously replicating sequence or origin of replication, and (b) sequences to terminate transcription. These elements are well known and their construction is within the skill of the ordinary artisan. If the metal ion regulating region is used independently, a non-MT promoter should be present in the vector to control gene expression. The gene to be expressed will be ligated to the MT TCS or in the alternative, the MT inducer plus exogenous promoter, in such a way as to place the gene under the transcriptional control of the TCS or the inducer-exogenous promoter combination.

The following disclosure is intended to serve as a representation of embodiments herein, and should not be construed as limiting the scope of this application.

GLOSSARY OF EXPERIMENTAL MANIPULATIONS

In order to simplify the Examples certain frequently occurring methods will be referenced by shorthand phrases.

Plasmids are designated by a small p preceded and/or followed by capital letters and/or numbers. The starting plasmids herein are commercially available, are available on an unrestricted basis, or can be constructed from such available plasmids in accord with published procedures.

"Klenow treatment" refers to the process of filling in a recessed 3' end of double stranded DNA with deoxyribonucleotides complementary to the nucleotides making up the protruding 5' end of the DNA strand. This process is usually used to fill in a recessed end resulting from a restriction enzyme cleavage of DNA. This creates a blunt or flush end, as may be required for further ligations. Treatment with Klenow is accomplished by reacting (generally for 15 minutes at 15° C.) the appropriate complementary deoxyribonucleotides with the DNA to be filled in under the catalytic activity (usually 10 units) of the Klenow fragment of *E. coli* DNA polymerase I ("Klenow"). Klenow and the other reagents needed are commercially available. The procedure has been published extensively. See for example T. Maniatis et al. 1982, Molecular Cloning, pp. 107–108.

"Digestion" of DNA refers to catalytic cleavage of the DNA with an enzyme that acts only at certain locations in the DNA. Such enzymes are called restriction enzymes, and the sites for which each is specific is called a restriction site. "Partial" digestion refers to incomplete digestion by a restriction enzyme, i.e., conditions are chosen that result in cleavage of some but not all of the sites for a given restriction endonuclease in a DNA substrate. The various restriction enzymes used herein are commercially available and their reaction conditions, cofactors and other requirements as established by the enzyme suppliers were used. Restriction enzymes commonly are designated by abbreviations composed of a capital letter followed by other letters and then, generally, a number, this abbreviation representing the microorganism from which each restriction enzyme originally was obtained. In general, about 1 µg of plasmid or DNA fragment is used with about 1 unit of enzyme in about 20 µl of buffer solution. Appropriate buffers and substrate amounts for particular restriction enzymes are specified by the manufacturer. Incubation times of about 1 hour at 37° C. are ordinarily used, but may vary in accordance with the supplier's instructions. After incubation, protein is removed by extraction with phenol and chloroform, and the digested nucleic acid is recovered from the aqueous fraction by precipitation with ethanol. Digestion with a single restriction enzyme optimally is followed with bacterial alkaline phosphatase hydrolysis of the terminal 5' phosphates to prevent the two termini from "circularizing" or forming a closed loop that would impede insertion of another DNA fragment at the restriction site. Unless otherwise stated, digestion of plasmids is followed by 5' terminal dephosphorylation. Procedures and reagents for dephosphorylation are conventional (T. Maniatis et al., Id., pp. 133-134).

"Recovery" or "isolation" of a given fragment of DNA from a restriction digest means separation of the digest on 6 percent polyacrylamide gel electrophoresis, identification of the fragment of interest by molecular weight (using oligonucleotides of known molecular weight as markers), removal of the gel section containing the desired fragment, and separation of the gel from DNA. This procedure is known generally. For example, see R. Lawn et al., 1981, "Nucleic Acids Res." 9:6103-6114, and D. Goeddel et al., (1980) Nucleic Acids Res., 8:4057.

"Transformation" means introducing DNA into an organism wherein the DNA is replicated.

"Ligation" refers to the process of forming phosphodiester bonds between two double stranded nucleic acid fragments (T. Maniatis et al., Id., p. 146). Unless otherwise stated, ligation was accomplished using known buffers and conditions with 10 units of T4 DNA ligase ("ligase") per 0.5 µg of approximately equimolar amounts of the DNA fragments to be ligated. Plasmids from the transformants were prepared, analyzed by restriction mapping and/or sequenced by the method of Messing et al., 1981, "Nucleic Acids Res.", 9:309.

"Preparation" of DNA from transformants means isolating plasmid DNA from microbial culture. Unless otherwise stated, the alkaline/SDS method of Maniatis et al., Id. p. 90., was used.

"Oligonucleotides" are short length single or double stranded polydeoxynucleotides which were chemically synthesized by the method of Crea et al., 1980, "Nucleic Acids Res." 8:2331-2348 (except that mesitylene nitrotriazole was used as a condensing agent) and then purified on polyacrylamide gels.

"Primer repair" refers to the process in which a mutation is introduced into a DNA fragment by preparing an oligonucleotide primer containing the mutation but which is otherwise complementary to a portion of the DNA to be mutated, hybridizing the primer to a single strand of the DNA to be mutated, replicating the DNA with Klenow, and recovering the mutant strand. See Goeddel et al., Id., p. 4057-4074.

"Synthetic linkers" are short oligonucleotides containing one or more restriction enzyme sites which are used generally to facilitate subsequent manipulation of the DNA. They are ligated to DNA in conventional fashion in order to introduce into the DNA the restriction enzyme site carried by the linker.

SPECIFIC DESCRIPTION OF EXPERIMENTAL MANIPULATIONS

*E. coli* and yeast were transformed, respectively, by the CaCl$_2$ method of Mandel et al., 1970 "J. Mol. Biol. 53:154 and Hinnen et al., 1974, P.N.A.S., 75:1929 as modified: (a) 20 percent PEG 4000 (Baker) was used and (b) a one-half hour recovery step in a medium consisting of 1M sorbitol, 35 percent YEPD (yeast extract peptone plus dextrose), and 7 mM CaCl$_2$ was included before plating cells with regeneration agar onto a Petri plate containing 20 ml of bottom agar (182 g sorbitol, 20 g glucose, 6.7 g Yeast Nitrogen Base (Difco) and 30 g agar per liter of H$_2$O). Any auxotrophic requirements other than the selective marker were supplemented by adevine, uracil leucine or tryptophan (20 µg/ml each) added to the bottom agar. Plasmids were cloned and maintained by transforming *E. coli* K12 strain 294 (ATCC 31446) with the ligation mixture and culturing in LB medium (Davis et al., 1980, Advanced Bacterial Genetics: A Manual for Genetic engineering) containing 20 µg/ml ampicillin.

The sources of haploid yeast strains and of plasmids are shown in table 1.

TABLE 1

| Organism | Phenotype or relevant characteristic | Origin |
| --- | --- | --- |
| 20B-12 | CUP1$^R$, trp1, pep4-3; expression host; source of chelatin gene | ATCC 20626 |
| SF648 | prc1-1, ura3-52, leu2-3, leu2-112, ade2-1, cup 1$^S$; source of chelatin gene | DBY 746 crossed with a CUP1$^S$ yeast strain available from the Yeast Genetic Stock Center |
| DBY746 | Source of leu$^-$ phenotype | Yeast Genetic Stock Center, University of California-Berkeley. |
| YEpIPT | Yeast expression vector | European Patent Application 88,632 |
| pHSA1 | Source of HSA gene | Lawn et. al., 1981, "Nucleic Acids Res." 9: 6103-6114 |
| pB1 | Source of PGK gene | Hitzeman et. al., 1980, "J. Biol. Chem." 255: 12073-12080 |
| YEp13 | Library vector | Broach et. al., 1979, "Gene" 8: 121-133; ATCC37115 |
| pUC 18 | Subcloning vector | Norrander et. al., 1983, "Gene" 26: 101-106 |

Yeast culture conditions are as described in Sherman et al., 1983, *Methods in Yeast Genetics*, Cold Spring Harbor Laboratory, using 0.67 percent Yeast Nitrogen Base without amino acids (Difco Labs) plus 2 percent glucose and sufficient amino acids and pyrimidines to supplement any auxotrophic markers as desired. 0.3 mM copper sulfate was added to culture media for copper induction and selection for copper resistance.

EXAMPLE 1

Manufacture of Vector Containing Inducible Chelatin Promoter

Genomic DNA was prepared from 20B12 by the method of Cryer, et al., 1975, in *Methods in Cell Biology*, ed. Prescott, D. M., vol. 12, p. 39–44. This DNA was partially digested with Sau3A and ligated to YEp13. The ligation mixture was used to transform SF648. Transformants were selected by growth on medium not containing leucine but supplementing other auxotrophic requirements, followed by selection on yeast culture medium containing 0.3 mM copper sulfate. Sequence data confirmed insertion of the chelatin gene into YEp13. A chelatin containing plasmid was designated p405 as shown in FIG. 1.

The construction of the expression vector is depicted in FIG. 1. YEpIPT was simultaneously digested with EcoRI and BamHI, and the 6.8 kb fragment recovered. The 375 bp BamHI-EcoRI 5' terminal fragment of the pBR322 tetracycline resistance gene was ligated to the 6.8 kb fragment of YEpIPT and the ligation mixture used to transform *E. coli* for weak (5 μg/ml) tetracycline resistance. Plasmids from a tetracycline resistant clone were designated YEp9T.

p405 was simultaneously digested with XbaI and RsaI, and the 0.2 kb fragment recovered. p405 was digested with SalI and XbaI and the 0.9 kb fragment recovered. These fragments, respectively, contain the chelatin metal ion regulatory region and a portion of the chelatin promoter.

YEp9T was digested simultaneously with EcoRI and SalI and the 6.5 kb vector fragment recovered.

A synthetic oligonucleotide linker was prepared having the sequence shown in FIG. 1. This linker supplies 18 bp of the promoter and 10 altered bases containing a unique EcoRI site to facilitate ligation to the HSA and PGK genes as shown below. The altered bases replace the 10 bp fragment 5'ATCACATAAA3' found in the wild type promoter immediately upstream from the chelatin start codon.

The synthetic linker, two chelatin TCS fragments and YEp9T digest were ligated as follows. pUC18 was digested simultaneously with XbaI and EcoRI and the 2.7 kb fragment recovered. This fragment was ligated simultaneously to the chelatin promoter RsaI-XbaI fragment and the synthetic linker described above, the ligation mixture was used to transform *E. coli* and transformants were selected by growth on media containing 20 μg/ml ampicillin.

Plasmid DNA was recovered from the transformants, digested sequentially with EcoRI and XbaI, and the 230 bp fragment containing the synthetic linker residue ligated to the RsaI-XbaI promoter was recovered. Note that the initial digestion with EcoRI serves to destroy the XbaI site, so that it is not necessary to conduct an XbaI partial digest. The recovered EcoRI-XbaI fragment then was ligated with the XbaI-SalI fragment containing the chelatin inducer into the YEpT vector fragment. The ligation mixture was used to transform *E. coli*. An ampicillin resistant colony contained p432. This plasmid contained the chelatin TCS in proper orientation, but was free of any coding sequences for chelatin.

EXAMPLE 2

Figure 2:
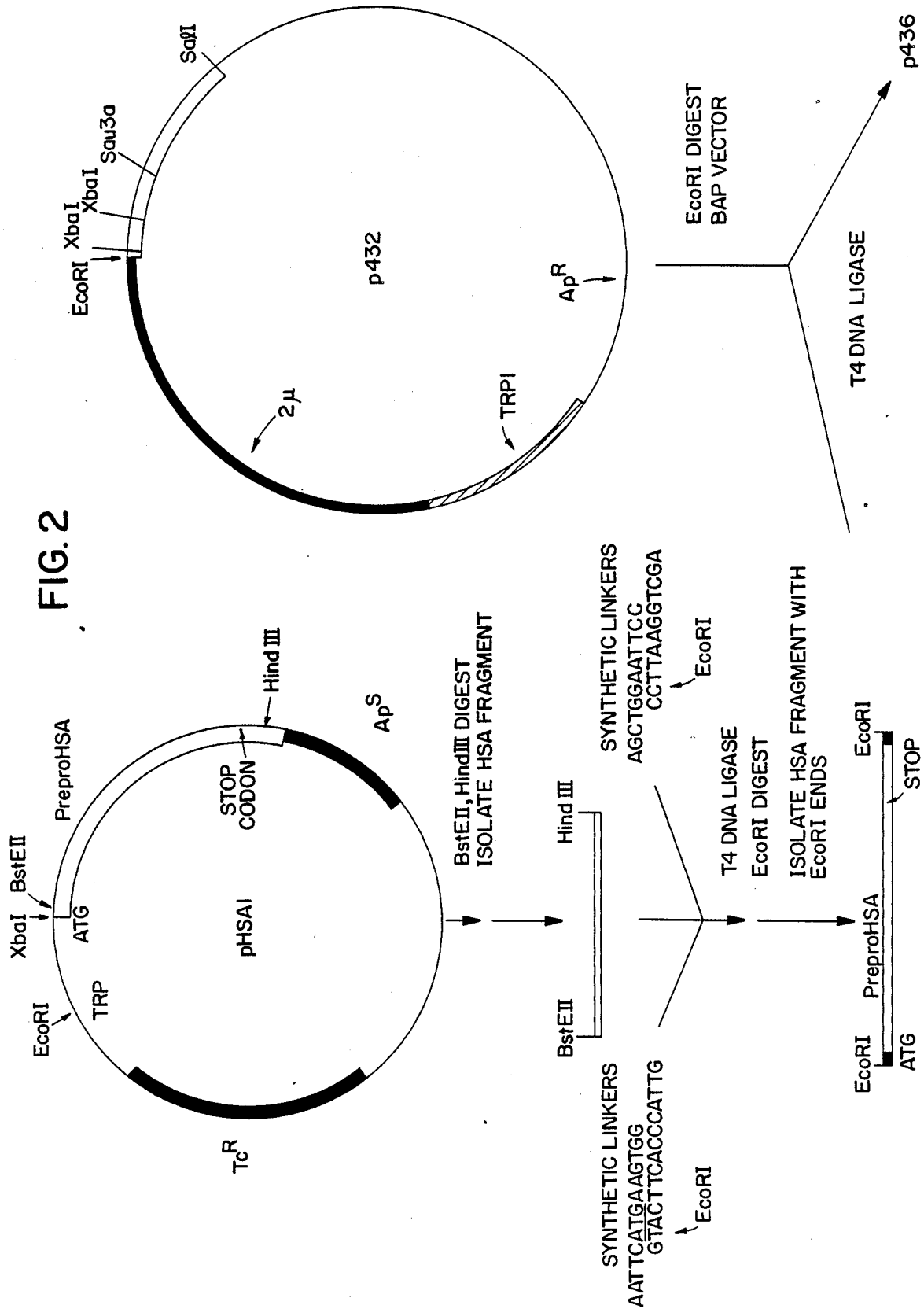
FIG. 2 and 3, respectively, show ligation of the FIG. 1 vector to the genes for prepro HSA (human serum albumin) and PGK (3-phosphoglycerate kinase).

Manufacture of a Vector Containing the HSA Gene Under Control of the Chelatin TCS This construction is shown in FIG. 2.

pHSA1 contains the entire coding region for prepro HSA (hereafter "HSA"). This plasmid was digested with BstEII and HindIII, and the 1.89 kb HSA fragment recovered. This fragment was ligated to the polynucleotide kinase phosphorylated synthetic linkers shown in FIG. 2 in order to flank the fragment with EcoRI sites. Concatamers which might inadvertently form during processing of the EcoRI sites-containing fragment could be digested with EcoRI. EcoRI sticky ends were generated by digesting the ligated mixture with EcoRI.

p432 was digested with EcoRI and treated with bacterial alkaline phosphatase in order to stably linearize the plasmid, the HSA EcoRI fragment ligated to the linearized plasmid and the mixture used to transform *E. coli*. Proper orientation was confirmed by PvuII restriction digests. A plasmid containing HSA under the control of the chelatin TCS was identified as p436.

EXAMPLE 3

Figure 3:
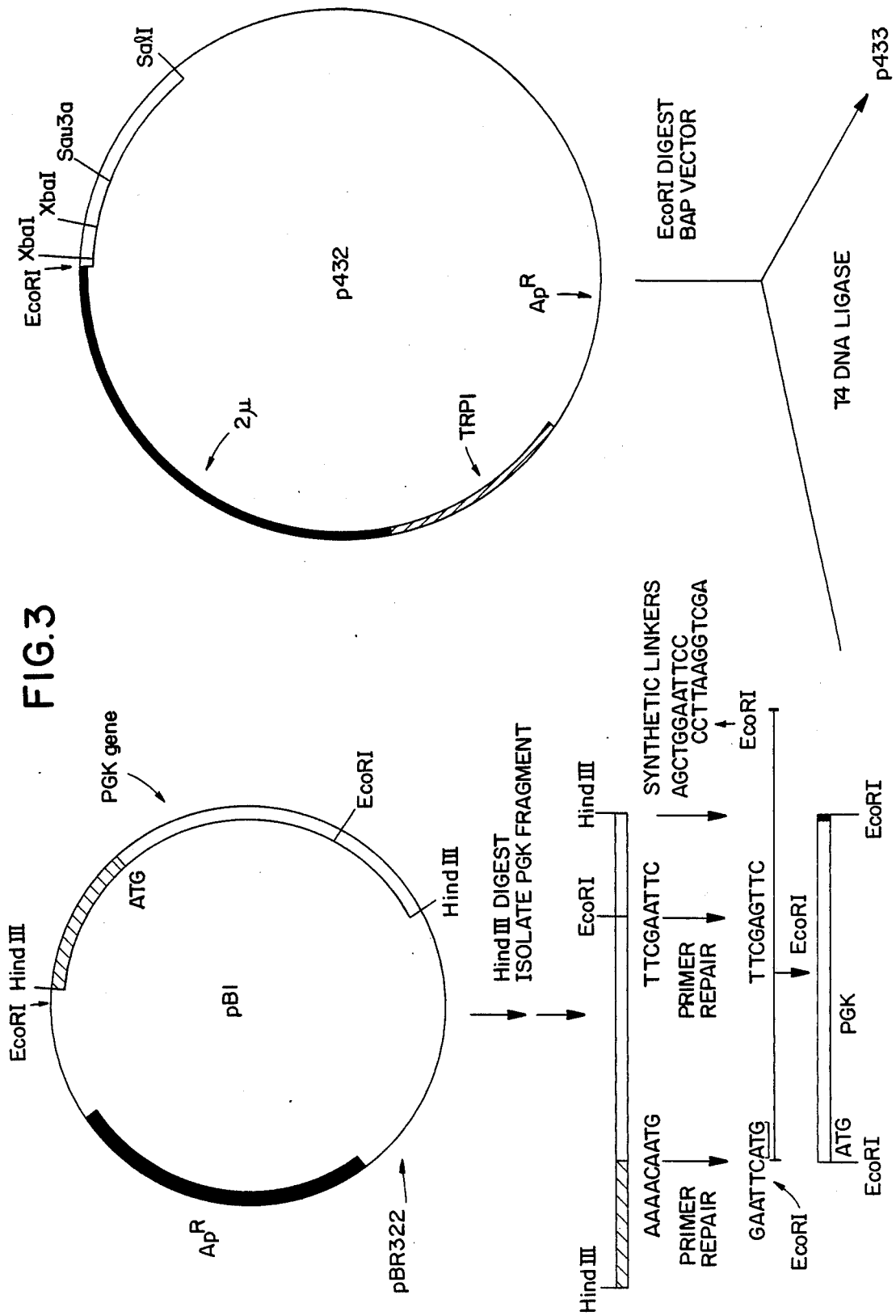

Manufacture of a Vector Containing the PGK Gene Under Control of the Chelatin TCS This construction is shown in FIG. 3.

pB1 was digested with HindIII and the 1.5 kb PGK fragment recovered. Primer repair was employed to introduce an EcoRI site in the 6 bp directly preceeding the PGK translational start codon. A primer oligonucleotide having the sequence 5' CTAGGCGAATT-CATGTCTT TATCT 3' was annealed to the 1.5 kb HindIII—HindIII fragment made single stranded by melting, treated with Klenow and mutant DNA recovered in accordance with the general method of primer repair (Goeddel et al., Nucleic Acid Res. 8: 4057–4074).

Primer repair also was used to delete an EcoRI site in the PGK structural gene. The primer, which was 5' GTGTTTTCGAATCCAAAAGT 3', was employed in the same fashion as described above, except that the single stranded template was the primer repaired DNA obtained in the preceeding step.

Finally, a polynucleotide kinased synthetic linker containing an EcoRI site was ligated to the 3' HindIII site of the PGK gene. The primer repaired DNA obtained as described in the two preceeding steps was digested with EcoRI and HindIII, the 1.5 kb fragment recovered and ligated to the synthetic linker shown in FIG. 3. The ligated fragment was digested with EcoRI in order to create sticky ends.

The EcoRI digested PGK gene was ligated to EcoRI digested, bacterial phosphatase treated p432 expression vector. The ligation mixture was used to transform *E. coli*. Transformants having the proper orientation were identified by ClaI digests. An expression plasmid containing PGK under the control of the chelatin TCS was identified as p433.

EXAMPLE 4

Figure 4:
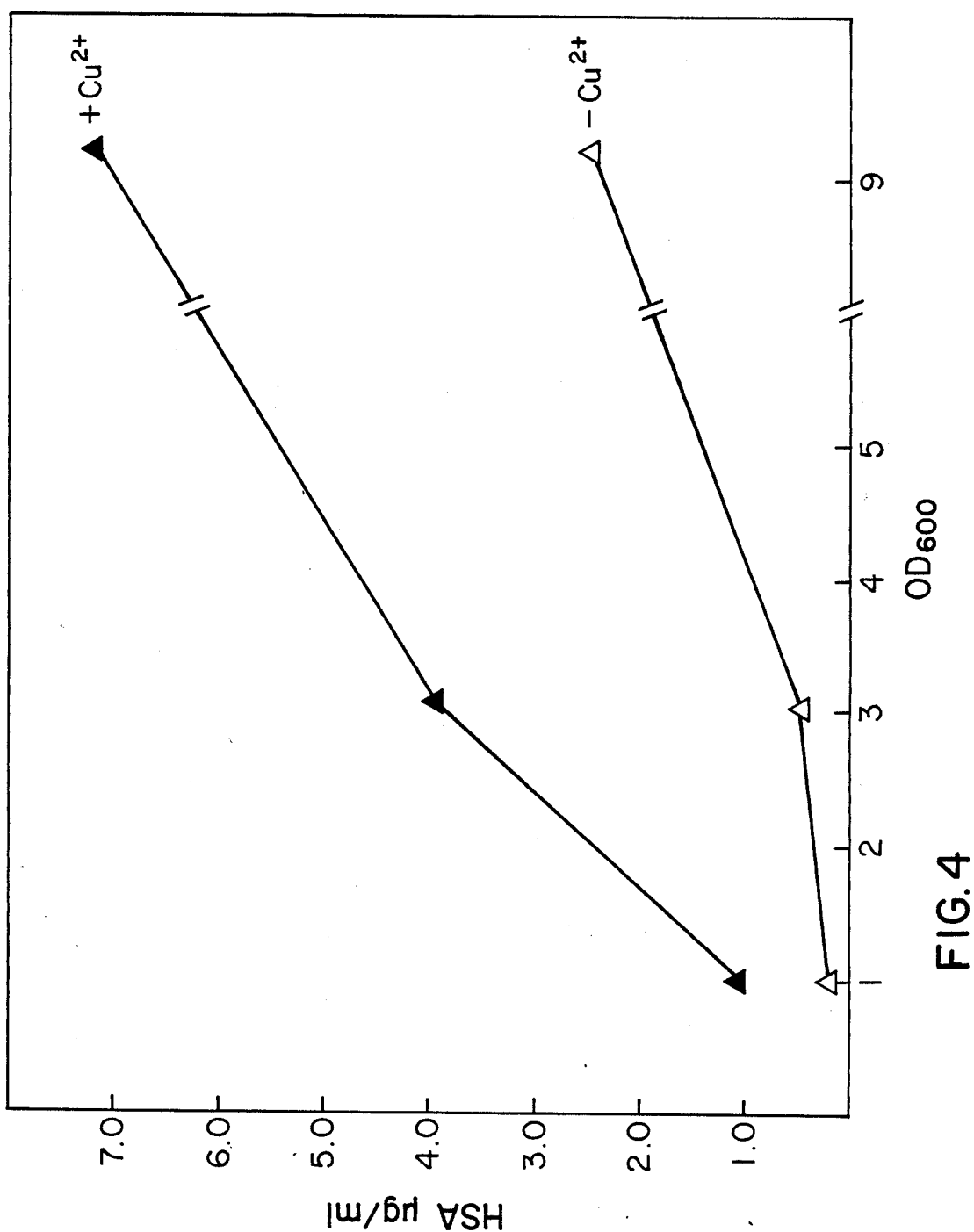
FIG. 4 demonstrates the induction of HSA by copper ions in p436 transformants.

Expression of HSA and PGK Under Control of the Chelatin TCS 20B-12 was transformed with either p436 or p433. Transformed 20B-12 was cultured for 18 hrs. at 30° C. in minimal medium with or without 0.3 mM copper sulfate until the OD of the culture increased to 9. Samples of the culture were taken at $OD_{600}=1$, 3 and 9, the cells concentrated by centrifugation, resuspended in one-fifth volume PBS+triton (150 mM NaCl, 20 mM sodium phosphate pH=7.9, 0,5 percent triton X-100) and an equal volume of glass beads, and vortexed at high speed for 4 minutes. This cell lysate was diluted into PBS+0.5 percent gelatin for quantitation by radioimmunoassay (HSA) or SDS sample buffer (Laemmli, 1970, "Nature" 227: 680) for quantitation by SDS gel analysis (PGK). FIG. 4 shows that the addition of copper to the culture medium as indicated results in a 5-fold increase in the HSA expressed, but that significant levels of HSA also were synthesized by the promoter in the absence of copper induction. HSA was present at 1 percent of the total cellular protein. Thus, the chelatin TCS was capable of both promoting and derepressing HSA synthesis in yeast.

Figure 5:
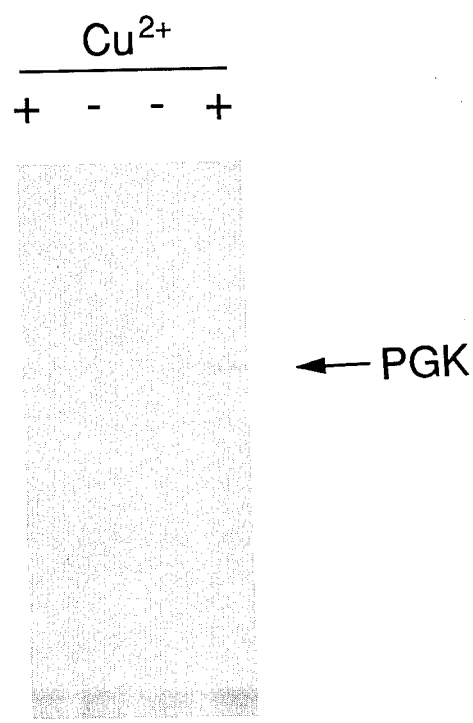
FIG. 5 demonstrates the induction of PGK by copper ions in p433 transformants.

The results with PGK were dramatic; >10 percent of total cell protein was PGK under derepressed conditions (see FIG. 5), whereas chelatin under these conditions is only present at 1 percent of cellular protein. The induction ratio of PGK (induced/repressed levels of PGK expression) is ten to twenty fold, indicating that the chelatin TCS is more effectively induced when expressing PGK than HSA. The chelatin TCS also is superior to glycolytic promoters (PGK) or alpha factor when expressing heterologous structural genes. Otherwise, PGK synthesis was similar to that of HSA.

We claim:

1. A vector comprising a selection gene, yeast origin of replication or autonomously replicating sequence and DNA encoding a eukaryotic polypeptide other than yeast chelatin, said DNA encoding a eukaryotic polypeptide that is under the control of (a) a yeast chelatin promoter, (b) a yeast chelatin transcription control sequence, or (c) a metal ion regulatory region of the yeast chelatin transcription control sequence which is free of the yeast chelatin promoter, whereby the vector is replicable in a suitable host.

2. The vector of claim 1 wherein the eukaryotic polypeptide is HSA, HBsAg, tPA, factor VIII, hGH, 3-phosphoglycerate kinase or lymphotoxin.

3. The vector of claim 1 wherein the yeast chelatin promoter is comprised within the −230 region from the chelatin start condon.

4. The vector of claim 1 wherein the yeast chelatin transcription control sequence is comprised within the −459 region from the chelatin start condon.

5. The vector of claim 1 wherein at least a portion of the metal ion regulatory region is comprised within the region extending from −230 to −459 of the chelatin start codon.

6. The vector of claim 1 wherein the DNA encoding a eukaryotic polypeptide is under the transcriptional control of the metal ion regulatory region of yeast chelatin free of the yeast chelatin promoter and additionally comprising a promoter other than the yeast chelatin promoter.

7. The vector of claim 6 wherein the promoter is a yeast promoter and the polypeptide is a mammalian protein.

8. The vector of claim 7 wherein the promoter is that of an invertase or glycolytic gene, acid phosphatase, α-factor or elongation factor I.

9. Yeast transformed with the vector of claim 1.

10. The yeast of claim 9 which is not copper sensitive.

11. A method comprising culturing the yeast of claim 9 and recovering said polypeptide from the yeast culture.

12. The vector claim 1 wherein the yeast chelatin promoter, the transcription control sequence, and the metal ion regulatory regions are from a Saccharomyces gene.

13. The vector of claim 12 wherein the Saccharomyces gene is the CUP1 gene.

14. An isolated DNA sequence comprising a yeast chelatin metal ion regulatory region free of the yeast chelatin promoter and free of DNA encoding yeast chelatin.

* * * * *